United States Patent
Stratienko

(12) 
(10) Patent No.: US 6,245,045 B1
(45) Date of Patent: Jun. 12, 2001

(54) COMBINATION SHEATH AND CATHETER FOR CARDIOVASCULAR USE

(76) Inventor: Alexander Andrew Stratienko, 1109 Centennial Dr., Chatta, TN (US) 37405

(*) Notice: Subject to any disclaimer, the term of this patent is extended or adjusted under 35 U.S.C. 154(b) by 0 days.

(21) Appl. No.: 09/296,581

(22) Filed: Apr. 23, 1999

(51) Int. Cl.$^7$ .................................................. A61M 5/178
(52) U.S. Cl. ................. 604/164.13; 604/167.02
(58) Field of Search ........................... 604/161.1, 170.03, 604/533, 532

(56) References Cited

U.S. PATENT DOCUMENTS

| | | |
|---|---|---|
| 3,875,938 | * 4/1975 | Mellor . |
| 4,270,535 | * 6/1981 | Bogue et al. . |
| 4,808,163 | 2/1989 | Laub . |
| 5,021,044 | 6/1991 | Sharkawy . |
| 5,180,364 | 1/1993 | Ginsburg . |
| 5,300,048 | 4/1994 | Drewes, Jr. et al. . |
| 5,380,276 | 1/1995 | Miller et al. . |
| 5,380,307 | 1/1995 | Chee et al. . |
| 5,425,723 | 6/1995 | Wang . |
| 5,480,392 | 1/1996 | Mous . |
| 5,569,197 | 10/1996 | Helmus et al. . |
| 5,599,324 | 2/1997 | McAlister et al. . |
| 5,709,874 | 1/1998 | Hanson et al. . |
| 5,738,666 | 4/1998 | Watson et al. . |
| 5,911,710 | * 6/1999 | Barry et al. . |

FOREIGN PATENT DOCUMENTS 0322225   6/1989   (EP) .

* cited by examiner

Primary Examiner—Mark Bockelman
(74) Attorney, Agent, or Firm—Chambliss, Bahner & Stophel, P.C.

(57) ABSTRACT

A vascular interventional device may be introduced over a guidewire into a vessel of the cardiovascular system of a patient. This device includes a hollow, flexible tube having a proximal end and a distal end that is adapted to selectively engage a target vessel of the cardiovascular system of the patient. This tube also includes a lumen that is continuous from the proximal to the distal end, and has an end hole in the distal end that is in fluid communication with the lumen. A plurality of side holes are provided near the distal end of the tube, each of which is in continuous fluid communication with the lumen. The device also includes a hollow vessel dilator that is adapted for insertion into and through the tube and over the guidewire. The dilator has an inside diameter that is slightly larger than the guidewire and an outside diameter that is slightly smaller than the diameter of the lumen of the tube. The distal end of the dilator is adapted to accommodate vascular entry over the guidewire, and the dilator is adapted to dilate the vessel to accept the tube. The device also includes a hub at the proximal end of the tube. The hub includes an end port through which a second interventional device having an outside diameter smaller than the diameter of the lumen may be introduced into the lumen of the tube. The hub also includes a side port through which a fluid agent may be injected for delivery through the lumen and out the end hole and side holes of the tube. A sealing mechanism is also provided in the hub to prevent air from entering the tube and blood and other fluids from leaking out of the tube through the hub. A pair of vascular interventional devices, at least one of which is constructed according to the invention, may be utilized to treat or study a cardiovascular condition, or to measure the blood pressure across a vascular segment.

21 Claims, 8 Drawing Sheets

COMBINATION SHEATH AND CATHETER FOR CARDIOVASCULAR USE

FIELD OF THE INVENTION

This invention relates generally to a vascular interventional device that may be introduced over a guidewire into a vessel of the cardiovascular system of a patient. More particularly, the invention relates to such a device that functions both as a vascular entry sheath and as a diagnostic or therapeutic catheter. Such a device is capable of delivering both diagnostic and/or therapeutic agents, as well as other interventional devices, to a specific target portion of the cardiovascular system of a patient.

EXPLANATION OF TECHNICAL TERMS

As used herein, a vascular interventional device or interventional device is any device that may be passed through a portion of the cardiovascular system of a patient for diagnostic or therapeutic purposes, including diagnostic and therapeutic catheters. The term also includes components of such devices and other instruments that may be used to facilitate the passage of such devices within the cardiovascular system, such as guidewires, dilators and sheaths.

As used herein, a patient may be a human or another mammal.

As used herein, vessels of the cardiovascular system of a patient or blood vessels include arteries and veins and branches thereof or therefrom, and other tubes, chambers and ducts that carry blood.

As used herein, a vessel of entry is a vessel that is entered from outside the body of the patient.

As used herein, a target vessel or branch of a vessel is a portion of the cardiovascular system of a patient that is targeted for diagnosis or therapy, or that provides a pathway to such portion from a vessel of entry. A target vessel may also be a vessel of entry.

As used herein, a vascular segment is a portion of a vessel.

As used herein, a vascular interventional device or a component thereof may be adapted to selectively engage a target vessel or branch of a vessel. Such a device or component may be shaped, formed or manipulated so that when it is advanced to a location adjacent to the target vessel or branch, further advancement will cause the distal end of the device to enter the target vessel or branch.

As used herein, a guidewire is a device that may be used in positioning and moving a diagnostic or therapeutic vascular interventional device.

As used herein, a sheath is a tube that may be used to facilitate the passage of a vascular interventional device within the cardiovascular system of a patient.

As used herein, a dilator is a vascular interventional device or a component thereof that may be used to dilate a portion of one or more vessels of the cardiovascular system so as to facilitate entry or passage of another vascular interventional device or component thereof.

As used herein, a catheter is a vascular interventional device that may be used for diagnostic or therapeutic purposes.

As used herein, a fluid agent is a drug or other fluid that may be injected into a portion of the cardiovascular system for therapeutic or diagnostic purposes.

As used herein, a fluid agent is delivered to a target portion of the cardiovascular system of a patient at a clinically effective rate or an effective rate when said agent is delivered at a flow rate that is suitable for the effective use of the fluid agent and at a velocity that is unlikely to cause injury or damage to the target portion of the cardiovascular system.

As used herein, a contrast agent, medium or fluid is a radiopaque fluid agent that may be used to provide a contrast in density with tissue, structures or another object for x-ray or other radiological examination.

As used herein, the French scale is a measurement system that may be used to indicate the diameter of a vascular interventional device or a component thereof. Each unit on the scale is equal to $1/\pi$, millimeters.

BACKGROUND AND DESCRIPTION OF THE PRIOR ART

In conventional practice, access to a vessel of the cardiovascular system of a patient may be obtained using a vascular entry sheath. Generally, a needle is used to puncture a blood vessel of entry (such as an artery), and a guidewire is passed through the needle to a desired location in the vessel. The needle is withdrawn and the guidewire is maintained in position in the vessel. Then a short sheath is advanced into the vessel over the guidewire to facilitate introduction of a diagnostic or therapeutic catheter. A catheter is advanced through the sheath, and the guidewire may then be removed. Once the distal end of the catheter is advanced to the target vessel, diagnostic or therapeutic procedures may be carried out. Depending on the type of catheter employed, fluid agents may be injected through the catheter for diagnostic or therapeutic purposes. However, if it is necessary or desirable to inject an x-ray contrast agent into a target vessel, a large caliber catheter must be advanced through the sheath to the target vessel, so as to provide for sufficiently high flow rates to displace blood with contrast agent. In most cases, the sheath itself may not serve as the conduit for delivery of contrast agent because conventional sheaths are usually quite short and are not adapted to selectively engage a vessel of the cardiovascular system. Furthermore, conventional sheaths have only a single end hole, and fluid injected therethrough in volumes sufficient for a contrast agent would likely flow from the end hole at such a velocity that tissue damage might occur. Consequently, a conventional sheath is used only to provide access to the vessel of entry, and a catheter is advanced through the sheath to reach a target vessel. If it is desired to deliver a fluid agent such as contrast fluid to a segment of the target vessel, it is generally necessary to employ a diagnostic catheter. If it is desired, after imaging of the target area, to employ another therapeutic or diagnostic device, the diagnostic catheter must first be removed, so that a second interventional device may be advanced to the target area.

Various catheters for distribution of fluid agents (sometimes referred to as infusion catheters) are known. For example, U.S. Pat. No. 5,021,044 of Sharkawy describes a vascular catheter having an inner lumen for receiving a guidewire and at least one concentrically disposed outer lumen for delivery of a fluid agent. The outer lumen is provided with a number of flow passageways to maintain a desired flow pattern to the target site, typically of about 0.1–1.5 cm$^3$/hour. U.S. Pat. No. 5,599,324 of McAlister et al. and U.S. Pat. No. 5,709,874 of Hanson et al. describe similar multi-lumen catheters. U.S. Pat. No. 5,380,307 of Chee et al. and U.S. Pat. No. 5,425,723 of Wang describe perfusion catheters that are designed to deliver a fluid agent through side holes uniformly along a perfusion portion of the catheter. These devices operate to deliver fluid to a target point within a vessel at low flow rates that are useful for introduction of pharmacological agents such as thrombolytic drugs, but are wholly insufficient for proper introduction of a contrast agent. Furthermore, these devices do not accommodate or facilitate the introduction of a second interventional device into the cardiovascular system of a patient.

U.S. Pat. No. 5,569,197 of Helmus et al. describes a hollow infusion guidewire over which a catheter may be introduced into a vessel. Preferably, the Helmus guidewire has an outer diameter that is comparable to that of a standard coronary guidewire, typically about 0.014 inch. It also has a plurality of openings or perforations in the sidewall near its distal end for dispersal of a drug therethrough. However, since it is sized to function as a guidewire too, it may only be used to disperse fluid at the target location at a very low rate, thereby limiting its use to the delivery of drugs only.

Many of the known infusion guidewires include complicated multi-lumenal structures and valve arrangements that are difficult and expensive to manufacture. Furthermore, these devices generally operate to deliver fluid agents to a target site at low flow rates that are wholly insufficient for use in delivering contrast media. Other devices that may be employed to deliver contrast media at an appropriate rate permit flow at a velocity that is likely to cause tissue damage. Thus, for example, U.S. Pat. No. 5,180,364 of Ginsburg describes a self-perfusing guiding catheter that is adapted for delivery of contrast media through a central lumen. The catheter includes a number of holes or slits that are provided with one-way valves so as to selectively permit fluid communication between the central lumen and the exterior of the device. When contrast media is injected through the central lumen, the valves close so that all of the contrast fluid is delivered out the end of the device. When no fluid is injected, the valves open to prevent the device from blocking blood flow within the vessel by permitting perfusing blood to flow into and through the catheter. After imaging of the target area is obtained, as by radiographic examination of the contrast media, a second catheter may be introduced through the central lumen and advanced to the target area. However, when the Ginsburg device is used to deliver a significant volume of contrast fluid in order to displace blood volume, the velocity of delivery of contrast fluid out the end hole may be so great that tissue damage may occur.

It would be desirable therefore if a vascular interventional device were developed that would be relatively simple and inexpensive to manufacture. It would also be desirable if such a device were developed that could be used to deliver fluid such as contrast media to a target area at a rate sufficient to displace blood so that a radiologic examination of the target area could provide useful information, but at a velocity that would minimize tissue damage. In addition, it would be desirable if such a device were developed that could be used to deliver fluid at an effective rate while a second interventional device was being used to diagnose or treat a condition.

OBJECTS AND ADVANTAGES OF THE INVENTION

Accordingly, it is an object of the invention claimed herein to provide a vascular interventional device that may be manufactured relatively easily and inexpensively. It is also an object of the invention to provide such a device which may be used to deliver a fluid agent to a target vessel or vessel segment at a clinically effective rate. Another object of the invention is to provide such a device that may also be used to deliver a second interventional device to a target vessel or vessel segment, which device may be used for therapeutic or diagnostic purposes while the fluid agent is being delivered at a clinically effective rate. It is yet another object of the invention to provide such a device that is adapted to selectively engage a target vessel of the cardiovascular system of a patient. It is still another object of the invention to provide a method for treating or studying a cardiovascular condition of a patient. It is yet another object of the invention to provide a method to measure the difference in blood pressure (if any) across a vascular segment of the cardiovascular system of a patient.

Additional objects and advantages of this invention will become apparent from an examination of the drawings and the ensuing description.

SUMMARY OF THE INVENTION

A vascular interventional device is provided that may be introduced over a guidewire into a vessel of the cardiovascular system of a patient. This device includes a hollow, flexible tube having a proximal end and a distal end, and a lumen that is continuous from the proximal to the distal end. An end hole in the distal end is in fluid communication with the lumen, and a plurality of side holes are provided near the distal end of the tube, each of which is in continuous fluid communication with the lumen. The distal end of the tube is adapted to selectively engage a target vessel of the cardiovascular system of the patient. The device also includes a hollow vessel dilator that is adapted for insertion into and through the tube and over the guidewire. The dilator has an inside diameter that is slightly larger than the guidewire, and an outside diameter that is slightly smaller than the diameter of the lumen of the tube. The distal end of the dilator is tapered to accommodate vascular entry over the guidewire. The dilator is adapted to dilate the vessel to accept the tube. The device also includes a hub at the proximal end of the tube. The hub includes an end port through which a second interventional device having an outside diameter smaller than the diameter of the lumen (including a second interventional device having a pressure transducer connected thereto) may be introduced into and through the lumen of the tube. The hub also includes a side port through which a fluid agent may be injected for delivery through the lumen and out the end hole and side holes of the tube, or through which pressures can be measured, using a pressure transducer that may be connected thereto. A sealing mechanism is also provided in the hub to prevent air from entering the tube and blood and other fluids from leaking out of the tube through the hub.

The invention also includes a method for treating or studying a cardiovascular condition of a patient, using two vascular interventional devices, at least one of which (a first vascular interventional device) includes a hollow, flexible tube, a hub and a dilator, as described above. According to this method, a guidewire is inserted into a vessel of the cardiovascular system of a patient in the conventional manner. The dilator of the first device is then inserted into the tube with its distal end protruding from the distal end of the tube. The dilator and tube are then inserted into the vessel over the guidewire and positioned in the target area. The dilator is then withdrawn through the tube from the cardiovascular system of the patient. A second interventional device is selected to treat or study the cardiovascular condition, and the second device is introduced through the end port of the hub of the first device. The second interventional device is advanced over the guidewire to the distal end of the tube of the first device, and the guidewire is then removed. A fluid agent is then injected through the side port for delivery through the lumen around the second vascular interventional device, and out the end hole and side holes of the tube. The second interventional device is employed to treat or study the cardiovascular condition.

The invention also includes a method for using a pair of vascular interventional devices to measure the difference in blood pressures across a vascular segment of the cardiovascular system of a patient. The method includes providing a first vascular interventional device that includes a hollow, flexible tube, a hub and a dilator, as described above. A guidewire is inserted into a vessel of the cardiovascular system of a patient in the conventional manner. The dilator of the first device is then inserted into the tube with its distal end protruding from the distal end of the tube. The dilator and tube are then inserted into the vessel over the guidewire and the distal end of the tube is positioned at a first location in the target area. The dilator is then withdrawn from the cardiovascular system of the patient and is removed from the tube. A first pressure transducer is attached to the side port of the first device. A second interventional device, which is suitable for use in measuring the blood pressure at a point in the cardiovascular system, is selected and introduced through the end port of the hub of the first device. The second interventional device is advanced over the guidewire so that its distal end is located at a second location beyond the first location (beyond the distal end of the tube of the first device). The guidewire is then removed, and a second pressure transducer is attached to the proximal end of the second interventional device. The blood pressure is then measured simultaneously at the distal end of the tube of the first interventional device (the first location) and at the distal end of the second interventional device (the second location). The difference in blood pressure, if any, between the first and second locations is then calculated.

In order to facilitate an understanding of the invention, the preferred embodiments of the invention are illustrated in the drawings, and a detailed description thereof follows. It is not intended, however, that the invention be limited to the particular embodiments described or to use in connection with the apparatus illustrated herein. Various modifications and alternative embodiments such as would ordinarily occur to one skilled in the art to which the invention relates are also contemplated and included within the scope of the invention described and claimed herein.

BRIEF DESCRIPTION OF THE DRAWINGS

The presently preferred embodiments of the invention are illustrated in the accompanying drawings, in which like reference numerals represent like parts throughout, and in which.

DESCRIPTION OF THE PREFERRED EMBODIMENTS OF THE INVENTION

Figure 1:
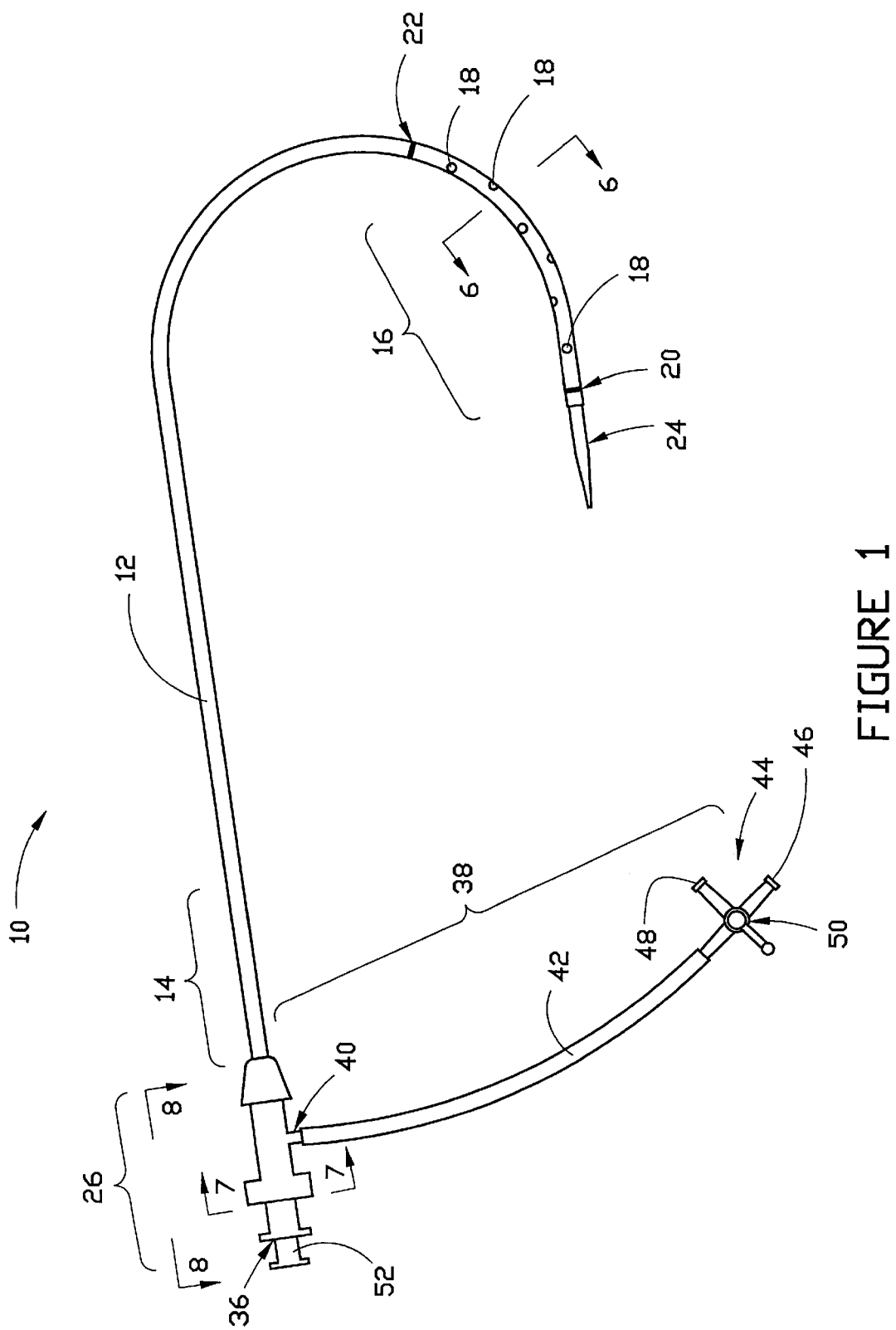
FIG. 1 is a plan view of a preferred embodiment of the invention.

Referring now to the drawings, FIG. 1 illustrates a preferred embodiment 10 of a vascular interventional device that may be introduced over a guidewire (not shown) into a vessel of the cardiovascular system of a patient. Generally, a needle (not shown) is used to puncture a blood vessel of entry (such as an artery), and a guidewire (also not shown) is passed through the needle to a desired location in the vessel. The needle is withdrawn and the guidewire is maintained in position in the vessel. Then the vascular interventional device 10 may be introduced into the vessel of entry over the guidewire, and guided or manipulated to a target vessel.

Figure 2:
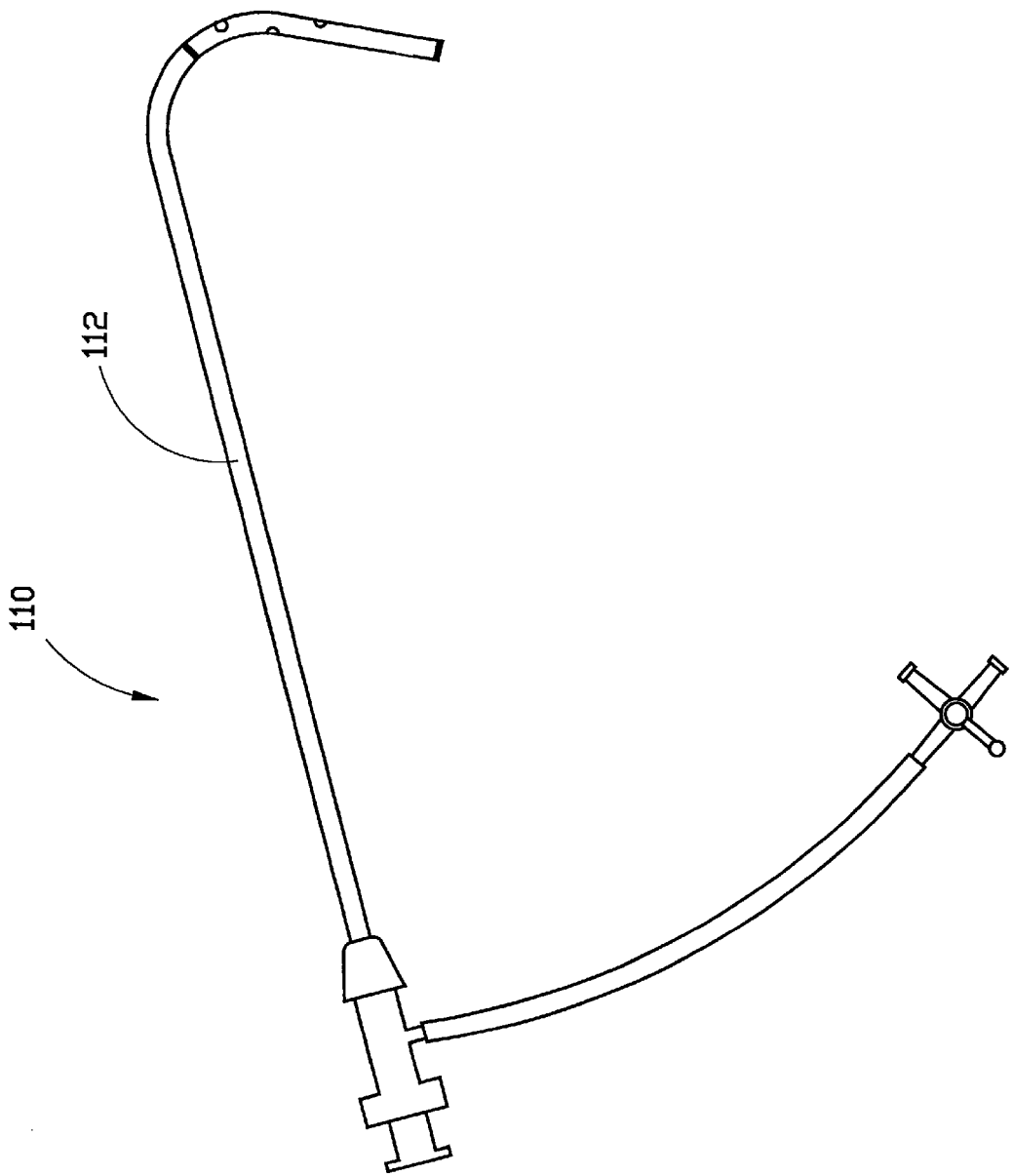
FIG. 2 is a plan view of a second embodiment of a portion of the invention.
Figure 3:
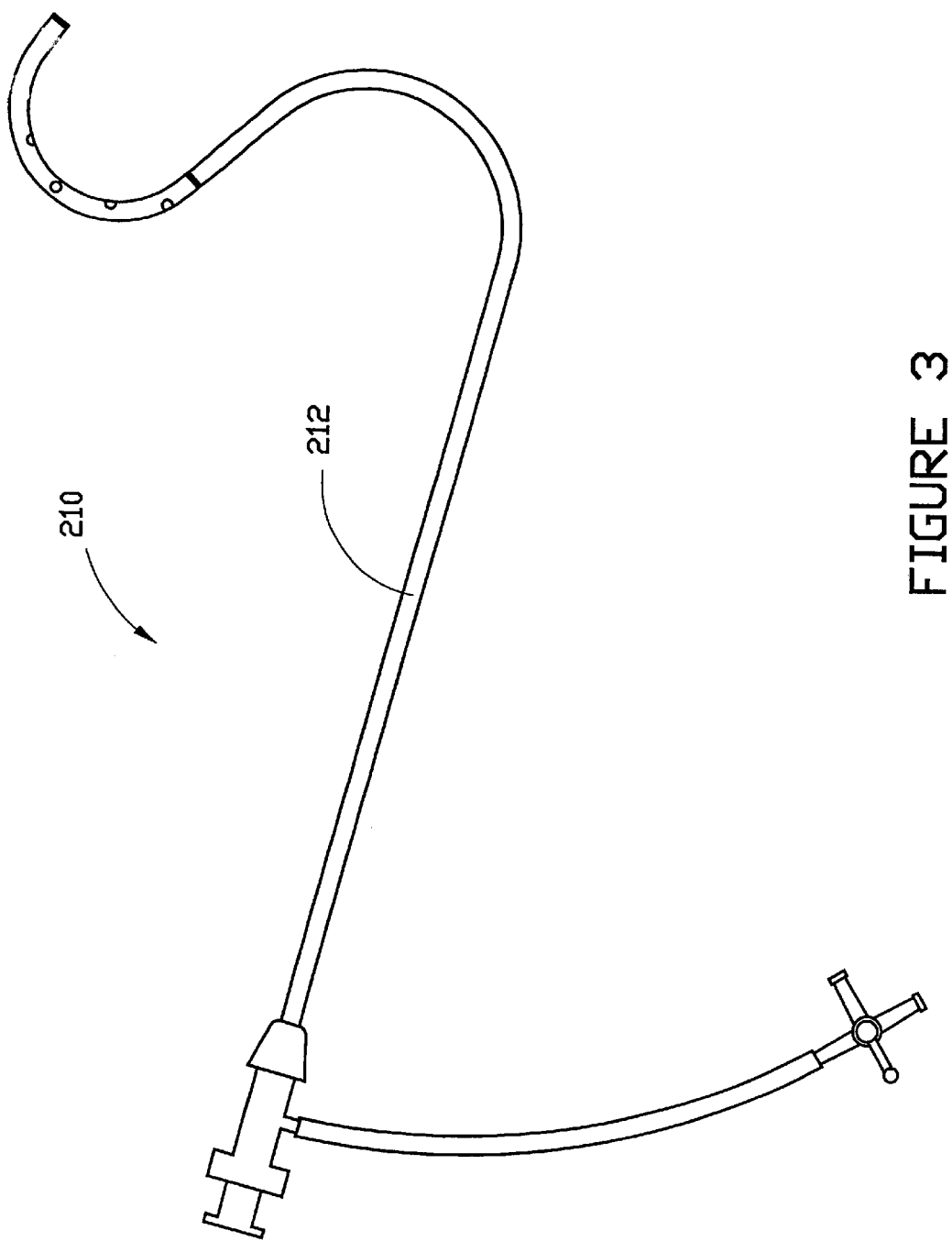
FIG. 3 is a plan view of a third embodiment of a portion of the invention.
Figure 4:
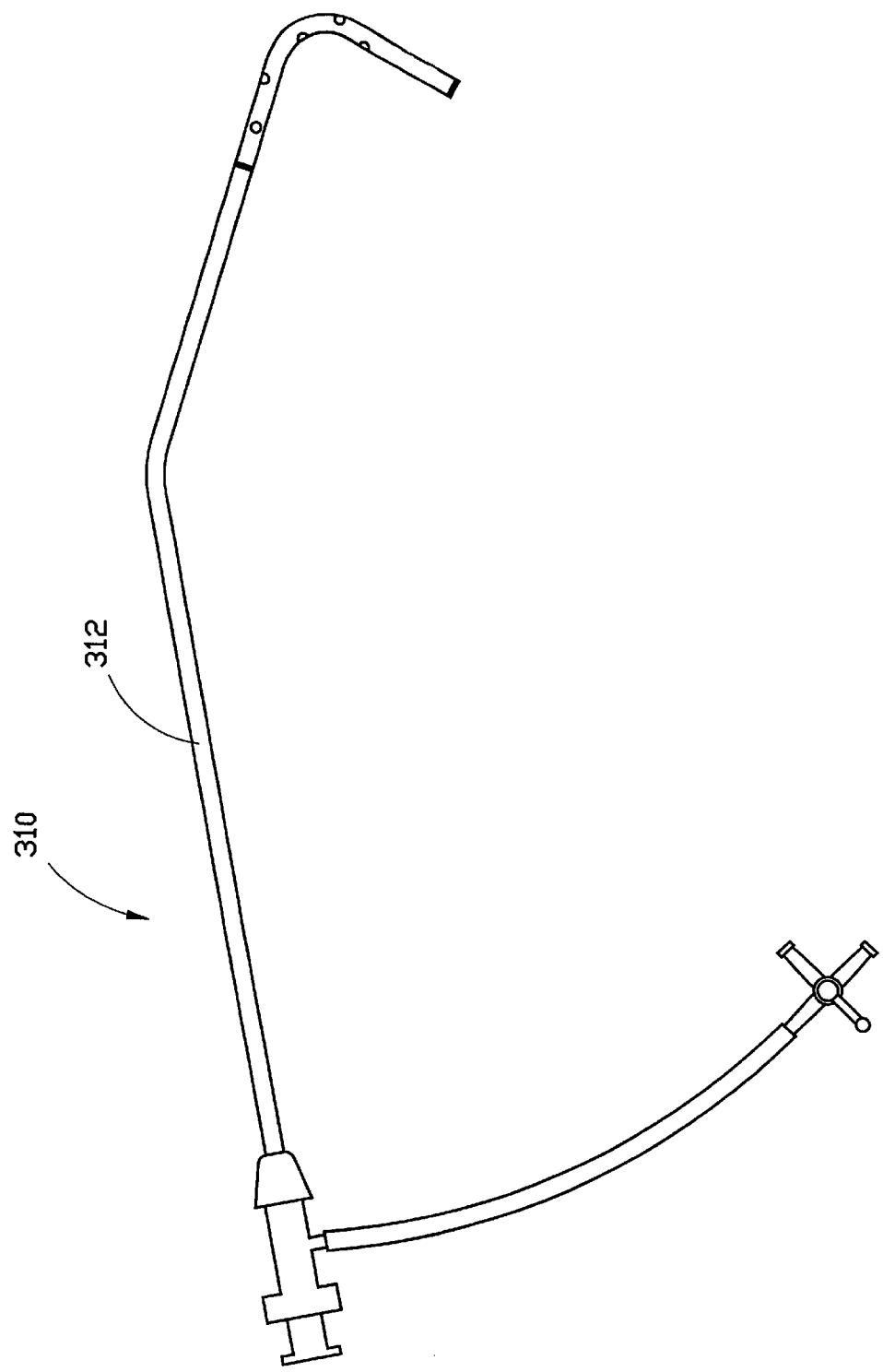
FIG. 4 is a plan view of a fourth embodiment of a portion of the invention.
Figure 5:
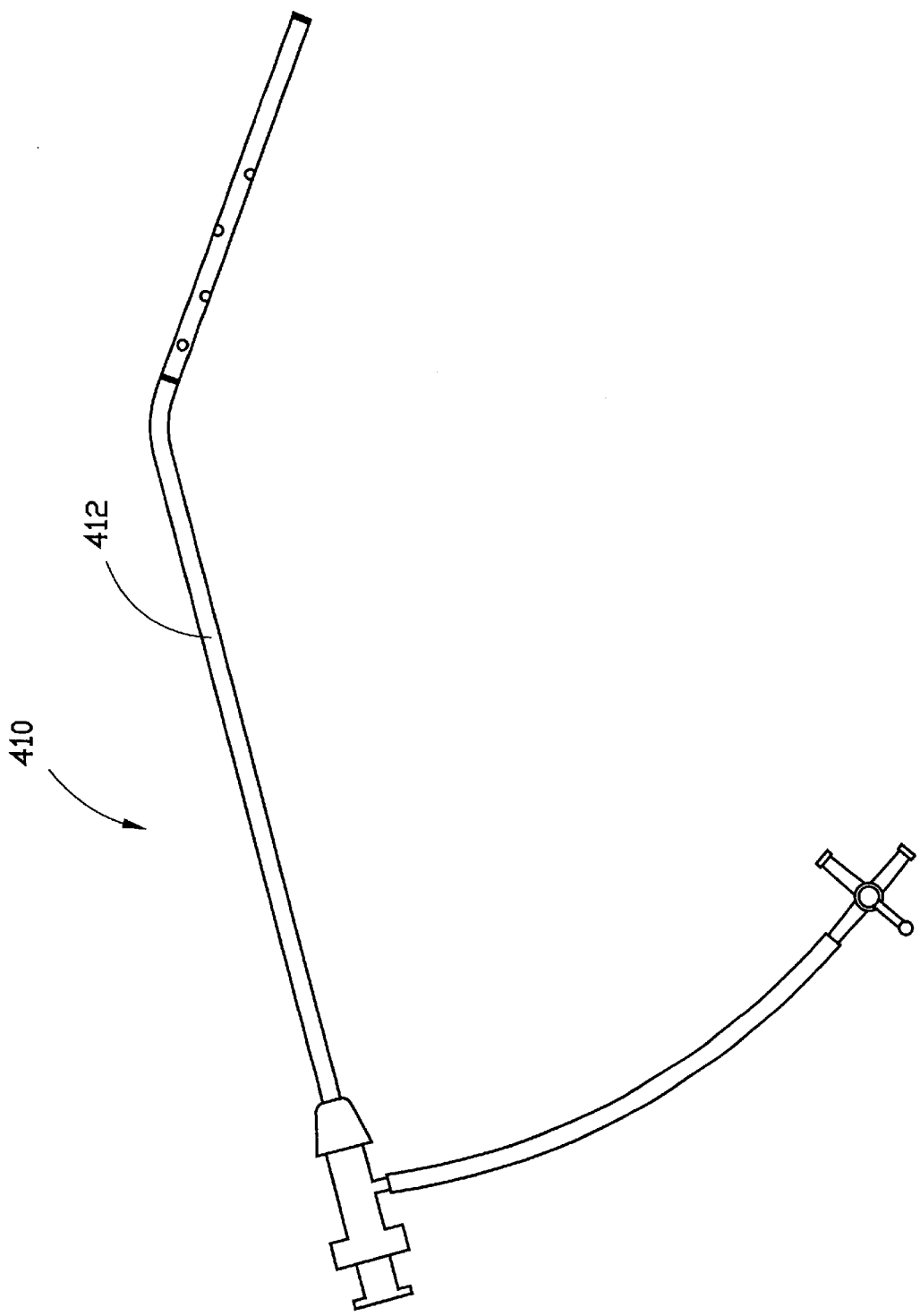
FIG. 5 is a plan view of a fifth embodiment of a portion of the invention.

Device 10 includes hollow, flexible tube 12 having proximal end 14 and distal end 16. Tube 12 is provided in any convenient length and diameter, depending on its intended use. The distal end of the tube is adapted to selectively engage a target vessel of the cardiovascular system of the patient. Such adaptation may be accomplished by providing the tube with a preformed shape of any convenient length and configuration. The tube may be straight, or it may be provided with curves of various radii, or with bends of varying angles, depending on the application for which it is intended. Preferably, the distal end of the tube is preformed so as to select a desired path into or through a vessel selected from the group consisting of common femoral arteries, profunda femoral arteries, superficial femoral arteries, common iliac arteries, internal iliac arteries, external iliac arteries, mesenteric arteries, renal arteries, gastric arteries, hepatic arteries, splenic arteries, pulmonary arteries, subclavian arteries, common carotid arteries, internal carotid arteries, external carotid arteries, innominate arteries and coronary arteries. Thus, for example, tube 12 of device 10 is provided with a preformed shape that is adapted to select a target vessel such as an iliac artery on one side of the patient's body, for example, from a vessel of entry such as the corresponding iliac artery on the other side of the body. By contrast, tube 112 of device 110, illustrated in FIG. 2, is provided with a preformed shape that is adapted to select a target vessel such as the superior mesenteric artery or the renal artery, for example, from a vessel of entry such as the common femoral artery. Similarly, tube 212 of device 210, illustrated in FIG. 3, is provided with a preformed shape that is adapted to select a target vessel such as the innominate artery or the carotid artery, for example, from a vessel of entry such as the common femoral artery. In addition, tube 312 of device 310, illustrated in FIG. 4, is provided with a preformed shape that is adapted to select a target vessel such as one of the renal arteries, for example, from a vessel of entry such as the common femoral artery. Another example is illustrated in FIG. 5, wherein tube 412 of device 410 is provided with a multipurpose preformed shape that is adapted to select any of a variety of target vessels from a vessel of entry.

Referring again to FIG. 1, tube 12 includes a lumen that is continuous from proximal end 14 to distal end 16, and an end hole in the distal end that is in fluid communication with the lumen. The tube is provided with a lumen having a diameter that is suitable for the intended use of device 10. Preferably, the tube has a minimum lumen diameter of about 3 on the French scale. Tube 12 also includes a plurality of side holes 18 near the distal end thereof, each of which is in continuous fluid communication with the lumen. Preferably, the tube includes at least one radiopaque marker at or near its distal end. Most preferably, two such markers are provided, marker 20 that is located at the distal end and marker 22 that is located adjacent to the side hole nearest the proximal end.

The device also includes a hollow vessel dilator that is adapted for insertion into and through the tube and over the guidewire. The dilator has an inside diameter that is slightly larger than the guidewire, and an outside diameter that is slightly smaller than the diameter of the lumen of the tube. By virtue of its size and shape, especially of distal tip 24 (illustrated in FIG. 1), the dilator is adapted to accommodate vascular entry over the guidewire, so that it may dilate the vessel of entry to accept the tube. Preferably, the distal tip of the dilator is preformed so as to select a desired path into or through a vessel of the cardiovascular system of the patient. It is also preferred that the dilator is adapted to be removable from the vessel through the tube after the tube has been inserted into the vessel.

Hub 26 is located at the proximal end of tube 12, and is attached thereto by force-fit, welding or other means known to those having ordinary skill in the art to which the invention relates. Hub 26 may be formed of polyethylene or other suitable material, and it may also be provided in several components, including attachment member 28A and secondary hub portion 29A (see FIG. 8), attachment member 28B and secondary hub portion 29B (see FIG. 9), or attachment member 28B and secondary hub portion 29C (see FIGS. 10 and 11). Preferably, tube 12 has a flared portion 30 at its proximal end and an annular shoulder 32 adjacent thereto that is adapted to provide a hub seat therebetween. Attachment member 28A or 28B of the hub is adapted to seat between flared proximal end 30 and shoulder 32 of the tube. In the embodiment of the hub illustrated in FIG. 8, a gasket, such as O-ring 34, may also be provided to seal the attachment member of the hub to the proximal end of the tube against leakage of blood or other fluid. In this embodiment, attachment member 28A is fixed to secondary hub portion 29A, and is adapted to rotate around the O-ring about axis 35 of tube 12 for purposes that will be subsequently explained. Other mechanisms for sealing against leakage of blood or other fluid between the attachment member of the hub and the proximal end of the tube, and for permitting rotation of at least a portion of the hub about axis 35 may also be provided. Two other alternative embodiments of the hub, illustrated in FIGS. 9 and 10–11, will also be described and explained.

Hub 26 includes end port 36 (see FIG. 1) through which a second interventional device (not shown) having an outside diameter smaller than the diameter of the lumen of tube 12 may be introduced through the end hole and into the lumen of the tube. Preferably, the hub is adapted to accommodate a second interventional device selected from the group consisting of guidewires, infusion guidewires, balloon angioplasty catheters, laser angioplasty catheters, rotational ablation catheters, atherectomy catheters, infusion catheters and diagnostic catheters.

Hub 26 also includes side port 38 (see FIG. 1), comprised of tube mount 40, side tube 42 and valve body 44, through which a fluid agent may be injected for delivery through the lumen and out the end hole and side holes of the tube. Valve body 44 includes a pair of entry ports 46 and 48 through which a fluid agent may be injected, and a valve 50 which may be operated to selectively open and close the entry ports.

Preferably, the dilator has a terminus 52 at its proximal end, which is mounted on the dilator so as to rotate thereabout. The terminus may be externally threaded through a portion thereof so as to be attached to mating internally threaded portion 54 (see FIGS. 8–11) within end port 36. In the alternative, the terminus may attach to the end port by snap fit or by other attachment means known to those having ordinary skill in the art to which the invention relates. When it is desired to remove the dilator from the cardiovascular system of a patient, the terminus is unthreaded from end port 36 so that the dilator may be removed through the tube.

Figure 7:
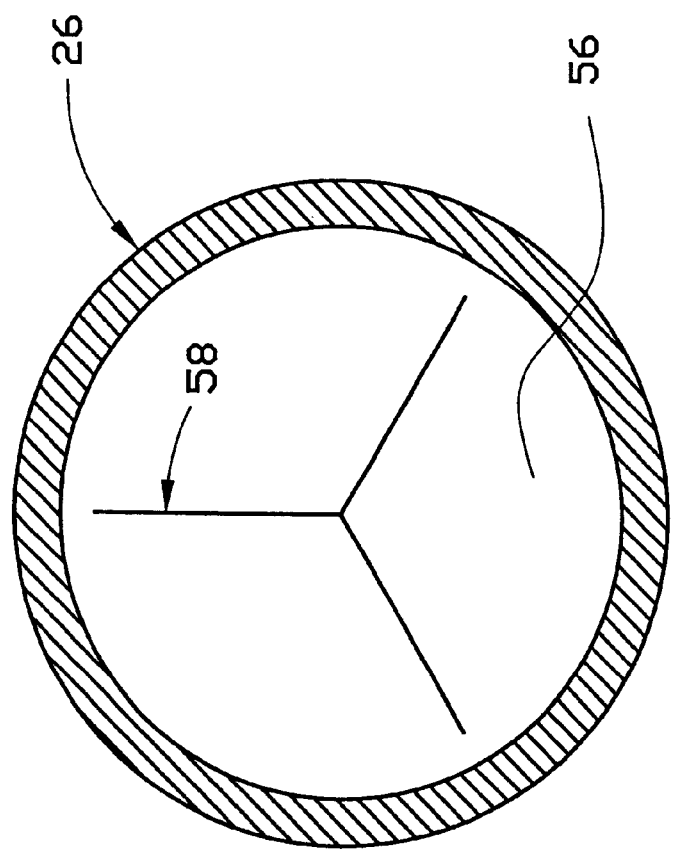
FIG. 7 is an enlarged sectional view of a portion of the device of FIG. 1, taken along the line 7—7 of FIG. 1.
Figure 6:
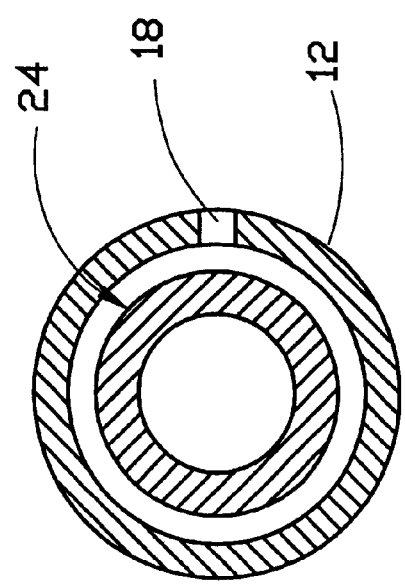
FIG. 6 is an enlarged sectional view of a portion of the device of FIG. 1, taken along the line 6—6 of FIG. 1.
Figure 9:
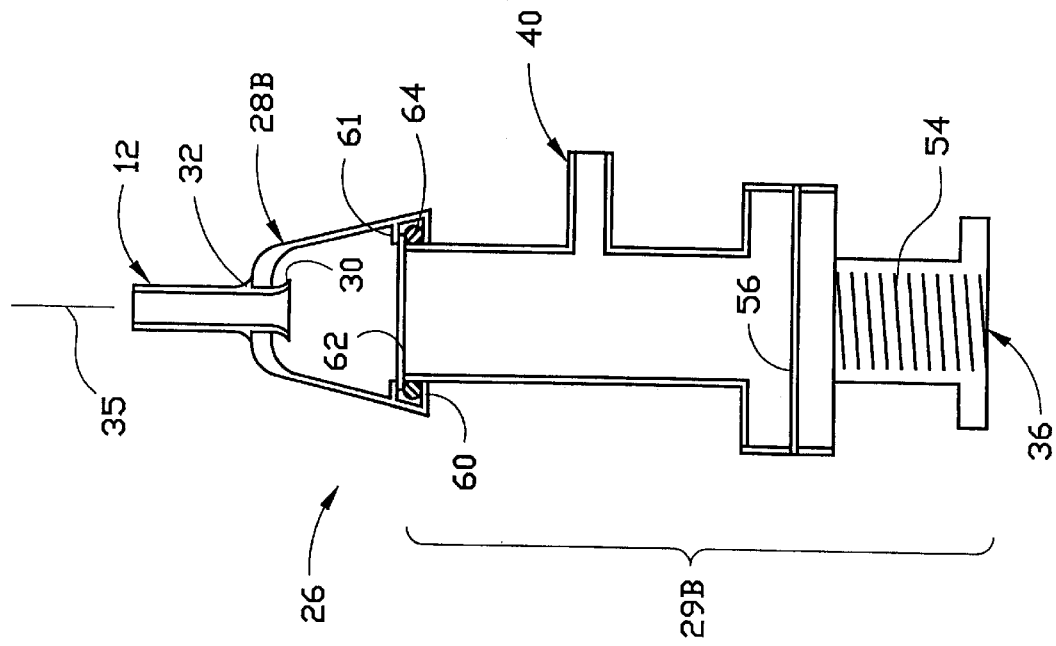
FIG. 9 is an enlarged sectional view of an alternative embodiment of the portion of the device illustrated in FIG. 8.
Figure 8:
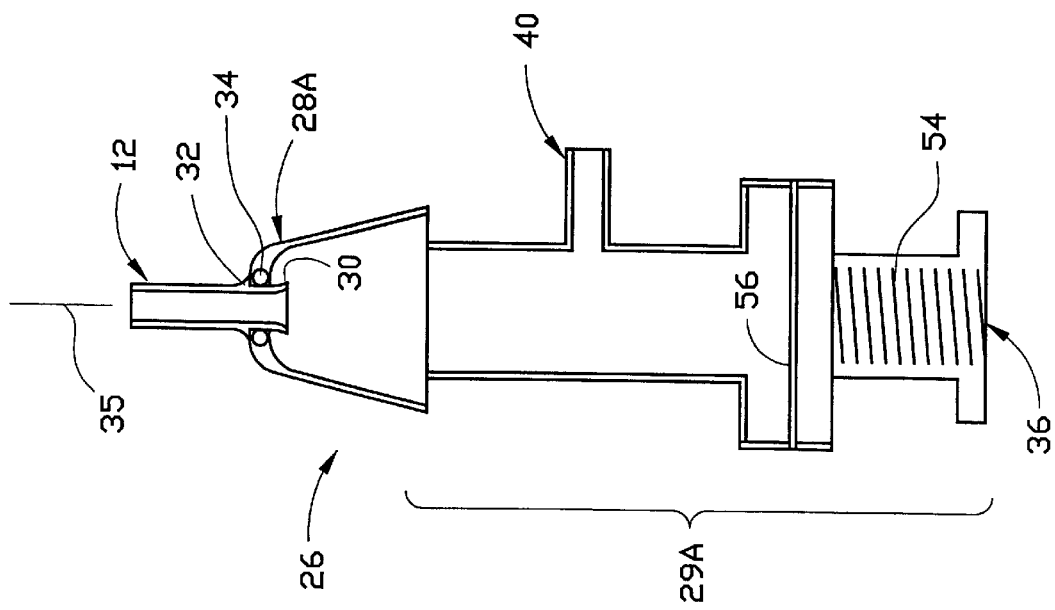
FIG. 8 is an enlarged sectional view of a portion of the device of FIG. 1, taken along the line 8—8 of FIG. 1.

Hub 26 also includes a sealing mechanism that prevents air from entering the tube and blood and other fluids from leaking out of the tube through the hub. The sealing mechanism may be used to seal the hub around a second interventional device that is in place in the hub, or it may seal the hub in the absence of such a device. In the embodiment of FIGS. 7–9, the sealing mechanism is provided in the form of diaphragm 56. Preferably, the diaphragm is provided in the form of a thin, flexible membrane of latex, silicone or other suitable material, with at least one and most preferably a series of slits 58 to permit the dilator or a second interventional device to be introduced therethrough. Preferably, the diaphragm prevents air from entering the tube and blood and other fluids from leaking out of the tube through the hub when the dilator is in place in the tube or when a second interventional device is introduced and advanced through the end port of the hub. The diaphragm will also preferably prevent air from entering the tube and blood and other fluids from leaking out of the tube through the hub when no dilator or second interventional device is in place in the tube. Another type of sealing mechanism, in the nature of a Touhy-Borst device, may also be used, as illustrated in FIGS. 10 and 11, which will be described in more detail hereinafter.

Preferably, side port 38 of hub 26 is adapted to rotate about the long axis of tube 12. This may be accomplished in several ways, three of which are illustrated in FIGS. 8, 9 and 10–11. As shown in FIG. 8, attachment member 28A and secondary hub portion 29A may be fixed together, and attachment member 28A may be adapted for rotation about tube 12 between flared portion 30 and shoulder 32. FIG. 9 illustrates a second embodiment of the hub, in which attachment member 28B is provided with an annular lip 60 at its lower end (as shown in FIG. 9), and retaining ring 61. Secondary hub portion 29B is also provided with an annular lip 62 at its upper end (as shown in FIG. 9) that may be retained within attachment member 28B and between its lip 60 and its retaining ring 61 so that side port 38 of the hub may rotate about axis 35 that extends generally along the length of the tube. Gasket 64 may be interposed between lip 60 of attachment member 28B and lip 62 of secondary hub portion 29B in order to seal the hub assembly against leakage of blood or other fluids.

Figure 10:
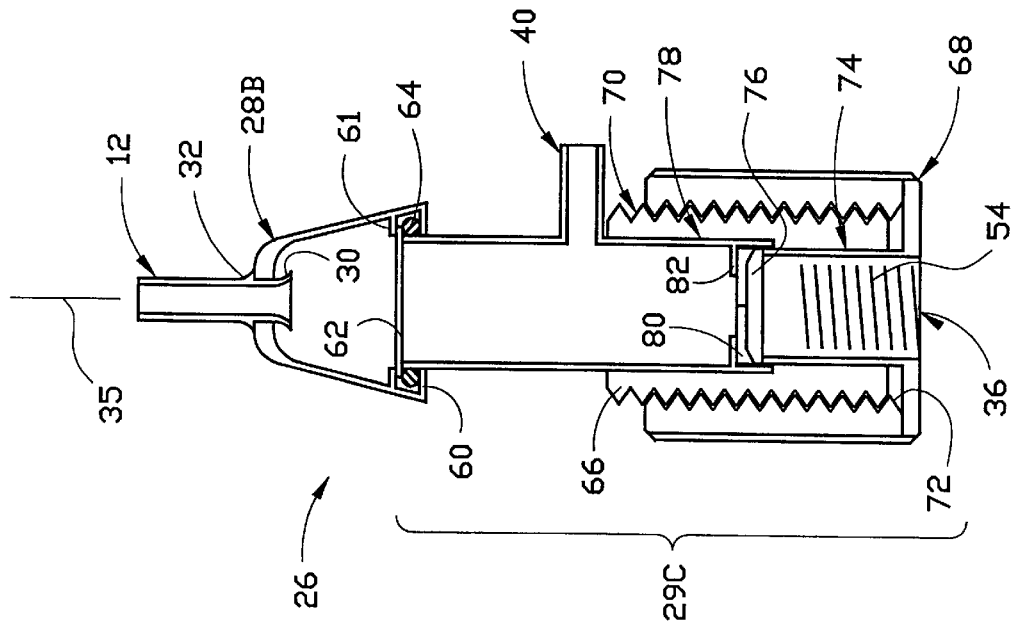
FIG. 10 is an enlarged sectional view of an alternative embodiment of the portion of the device illustrated in FIGS. 8 and 9, which employs a Touhy-Borst type sealing mechanism, illustrating the sealing mechanism in an open configuration.
Figure 11:
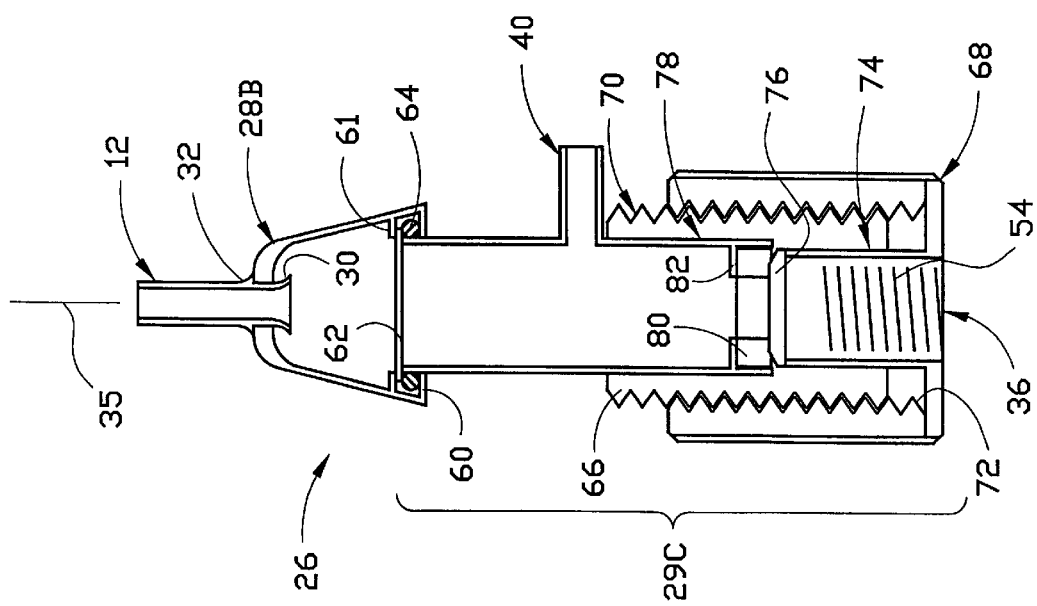
FIG. 11 is an enlarged sectional view of the portion of the device illustrated in FIG. 10, illustrating the sealing mechanism in an closed configuration.

FIGS. 10 and 11 illustrate a third embodiment of the hub which employs a Touhy-Borst type sealing mechanism. In this embodiment, secondary hub portion 29C is connected to attachment member 28B in the same manner as in the embodiment of FIG. 9 so that side port 38 of the hub may rotate about axis 35. Secondary hub portion 29C includes inner component 66 and outer component 68. Inner component 66 is externally threaded with threads 70. Outer component 68 is internally threaded with threads 72, which are adapted to mate with threads 70. Outer component 68 also includes inner cylinder 74, which is hollow and opens at its outer end into end port 36. Inner cylinder 74 is also internally threaded with threads 54 that are adapted to mate with terminus 52 of the dilator. At the inner end of cylinder 74 is washer 76, a generally rigid, circular washer having a central hole therethrough. Cylinder 74 of outer component 68 is adapted to move axially, as the outer component is threaded onto the inner component, into receiving cylinder 78 of the inner portion. Located within the receiving cylinder is a compressible gasket 80 which is provided with a central hole therethrough. Gasket 80 is retained within the receiving cylinder by end wall 82, which also has a central hole therethrough. When the hub of this embodiment is in the open configuration illustrated in FIG. 10, there is an open passageway from end port 36 through inner cylinder 74, washer 76, gasket 80, end wall 82 and the remainder of secondary hub portion 29C, attachment member 28B and into tube 12. A second interventional device may be passed through this passageway into the cardiovascular system of a patient. When outer component 68 is advanced by threading it further onto inner component 66, washer 76 atop cylinder 74 compresses gasket 80 against end wall 82 of receiving cylinder 78 so as to close its central hole to seal the hub to prevent air from entering the tube and blood and other fluids from leaking out of the tube through the hub. The sealing mechanism may be used to seal the hub around a second interventional device that is in place or in the absence of such a device.

Tube 12 and side tube 42 of device 10 may be formed from any suitable material known to those having ordinary skill in the art to which the invention relates, and the dilator may be formed from similar material. Preferably, these components are made primarily of a synthetic material, although they may include a reinforcing mesh of metal, glass fibers or the like, imbedded within the material of the tube. Good results may be expected when the tube is made primarily of a material selected from the group consisting of polytetrafluorethylene, polyolefin, polyester, polyethylene and conjugates of such materials. Preferably, at least a portion of the outside of the tube is coated with lubricious material, such as silicone, so as to facilitate entry and passage of the tube into and through the cardiovascular system of a patient.

The diameter of the lumen of the tube, and the number, shape and size of each of the side holes are such that a fluid agent may be delivered out the end hole and side holes of the tube at a rate and velocity sufficient to displace blood from the portion of the vessel in which the distal end of the tube resides without damaging such portion of the vessel. Preferably, the rate of flow out the end bole and side holes of the tube is at least about one cubic centimeter per second while a second interventional device is in place in the distal end of the tube. Preferred results may be obtained when six circular side holes, each having a diameter of about one millimeter, are provided in a spiral pattern around the periphery of tube at the distal end, and wherein the end hole of the tube has a diameter of at least about 3 on the French scale.

The invention can be used to perform any of several diagnostic and therapeutic procedures. For example, it can be employed in a method for treating or studying a cardiovascular condition of a patient. According to this method, a first vascular interventional device similar to device 10 is provided. A guidewire (not shown) is inserted into a vessel of the cardiovascular system of a patient in the conventional manner. The dilator of the first vascular interventional device is inserted into the tube of the first device so that its distal end protrudes from the distal end of the tube. The dilator and tube are then introduced over the guidewire into the vessel, and the distal end of the tube is advanced to a location of interest, such as the location of a blockage or partial blockage in the vessel. The dilator of the first device may then be withdrawn through the tube from the cardiovascular system of the patient, and a second interventional device (not shown), which may be used to treat or study the cardiovascular condition, may then be selected. This device may be a guidewire or another device such as a balloon angioplasty catheter, a laser angioplasty catheter, a rotational ablation catheter or an atherectomy catheter. If the second device is a guidewire, the first guidewire is removed from the cardiovascular system of the patient and the second introduced through the tube of the first device. Otherwise, the second interventional device may be introduced through the end port of the first device, and advanced over the guidewire until its distal end reaches a point in the target vessel beyond the distal end of the tube of the first vascular interventional device. A fluid agent, such as X-ray contrast agents, thrombolytic agents, anticoagulants and platelet aggregation inhibitors, may then be injected through the side port of the first device for delivery through the lumen around the second vascular interventional device, and out the end hole and side holes of the tube. It may be desired that the fluid agent, especially if it is an X-ray contrast agent, be delivered at a rate and velocity sufficient to displace blood from the portion of the vessel in which the distal end of the tube resides without damaging such portion of the vessel. Preferably, the rate of flow of an X-ray contrast agent out the end hole and side holes is at least about one cubic centimeter per second. If the fluid agent employed is an X-ray contrast agent, a radiographic imaging device may be employed to examine the target location in the vessel while the second interventional device is in place within the vessel. The second device may then be employed to treat or study the cardiovascular condition.

The invention can also be used in a method for measuring the difference in blood pressures across a vascular segment of the cardiovascular system of a patient. According to such method, a first vascular interventional device similar to device 10 is provided. The diameter of the lumen of the tube of this device, the number of side holes and the shape and size of each of the side holes are such that fluid communication may be maintained throughout the length of the tube while a second interventional device is in place in the distal end of the tube. According to this method, a guidewire is inserted into a vessel of the cardiovascular system of a patient in the conventional manner. The dilator of the first vascular interventional device is then inserted into the tube so that its distal end protrudes from the distal end of the tube. The dilator and tube are then introduced over the guidewire into the vessel, and the distal end of the tube is advanced to a first location of interest (such as a location adjacent to a partial blockage, aneurysm or other vessel anomaly). The dilator of the first device is then withdrawn from the cardiovascular system of the patient through and out of the tube of the first device, and a first conventional pressure transducer is attached to the side port of the first device. A second interventional device which is adapted to measure the blood pressure at a point in the cardiovascular system is selected and introduced through the end port of the hub of the first device. The distal end of the second interventional device is advanced over the guidewire to a second location that is beyond the first location (such as a location beyond a partial blockage, aneurysm or other vessel anomaly). The guidewire is removed from the cardiovascular system of the patient, and a second pressure transducer is attached to the proximal end of the second device. The blood pressure may then be measured simultaneously at the distal end of the tube of the first interventional device (the first location) and at the distal end of the second interventional device (the second location). The difference in blood pressure between the first and the second locations may also be calculated. Because the diameter of the lumen of the tube of the first interventional device, the number of side holes, and the shape and size of each of the side holes are such that fluid communication may be maintained throughout the length of the tube while a second interventional device is in place in the distal end of the tube, the pressure measurement taken at the first location may accurately represent the actual pressure at such location.

Although this description contains many specifics, these should not be construed as limiting the scope of the invention but as merely providing illustrations of some of the presently preferred embodiments thereof, as well as the best mode contemplated by the inventor of carrying out the invention. The invention, as described herein, is susceptible to various modifications and adaptations, and the same are intended to be comprehended within the meaning and range of equivalents of the appended claims.

What is claimed is:

1. A vascular interventional device that may be introduced over a guidewire into a vessel of the cardiovascular system of a patient, said device comprising:
    (a) a hollow, flexible tube having:
        (i) a proximal end;
        (ii) a distal end that is adapted to selectively engage a target vessel of the cardiovascular system of the patient;
        (iii) a lumen that is continuous from the proximal to the distal end;
        (iv) an end hole in the distal end thereof that is in fluid communication with the lumen; and
        (v) a plurality of side holes near the distal end thereof, each of which is in continuous fluid communication with the lumen;
    (b) a hub at the proximal end of the tube, said hub including:
        (i) an end port through which a second interventional device having an outside diameter smaller than the diameter of the lumen may be introduced into the lumen of the tube; and
        (ii) a side port through which a fluid agent may be injected for delivery through the lumen and out the end hole and side holes of the tube;
        (iii) a sealing mechanism that prevents air from entering the tube and blood and other fluids from leaking out of the tube through the hub;
    (c) a flexible, hollow vessel dilator that is adapted for insertion into and through the tube and over the guidewire, said dilator:
        (i) having a proximal end and a distal end, said distal end being adapted to accommodate vascular entry over the guidewire;
        (ii) having an inside diameter that is slightly larger than the guidewire;
        (iii) having an outside diameter that is slightly smaller than the diameter of the lumen of the tube;
        (iv) being adapted to dilate the vessel to accept the tube; and
        (v) being adapted for secure but removable attachment to the hub at its proximal end.

2. The device of claim 1 wherein the lumen diameter, the number of side holes and the shape and size of each of the side holes are selected so that a fluid agent may be delivered out the end hole and side holes of the tube at a rate of at least about one cubic centimeter per second while a second interventional device is in place in the distal end of the tube.

3. The device of claim 1 wherein the tube has a minimum lumen diameter of about 3 on the French scale.

4. The device of claim 1 which is adapted to accommodate a second interventional device selected from the group consisting of guidewires, infusion guidewires, balloon angioplasty catheters, laser angioplast catheters, rotational ablation catheters, atherectomy catheters, infusion catheters and diagnostic catheters.

5. The device of claim 1 wherein at least a portion of the outside of the tube is coated with lubricious material.

6. The device of claim 1 wherein the distal end of the tube is preformed so as to select a desired path into or through a vessel selected from the group consisting of common femoral arteries, profunda femoral arteries, superficial femoral arteries, common iliac arteries, internal iliac arteries, external iliac arteries, mesenteric arteries, renal arteries, gastric arteries, hepatic arteries, splenic arteries, pulmonary arteries, subclavian arteries, common carotid arteries, internal carotid arteries, external carotid arteries, innominate arteries and coronary arteries.

7. The device of claim 1 wherein the dilator includes a tip at its distal end, which tip is preformed so as to select a desired path into or through a vessel of the cardiovascular system of the patient.

8. The device of claim 1 wherein the dilator includes a terminus at its proximal end, which terminus is adapted to be attached to the hub.

9. The device of claim 1 wherein the tube has an axis along its length, and the side port of the hub is adapted to rotate about the axis of the tube.

10. The device of claim 9 wherein the hub includes an attachment member for attachment of the tube thereto, and a secondary hub portion to which the side port is attached, and wherein the attachment member and the secondary hub portion are adapted to rotate with respect to each other so that the side port may rotate about the axis of the tube.

11. The device of claim 1 wherein the tube includes at least one radiopaque marker at or near its distal end.

12. The device of claim 11 wherein the tube includes two radiopaque markers, one located at the distal end and the other located adjacent to the side hole nearest the proximal end.

13. The device of claim 1 wherein the tube is made primarily of a synthetic material.

14. The device of claim 13 wherein the tube is made primarily of a material selected from the group consisting of polytetrafluorethylene, polyolefin, polyester, polyethylene and conjugates of such materials.

15. The device of claim 13 wherein the tube includes a reinforcing mesh imbedded within the material of the tube.

16. The device of claim 1 wherein the sealing mechanism prevents air from entering the tube and blood and other fluids from leaking out of the tube through the hub when a second interventional device is introduced and advanced through the end port.

17. The device of claim 16 wherein the sealing mechanism is provided in the form of a diaphragm that is comprised of a flexible membrane having at least one slit for introduction of the second interventional device therethrough.

18. The device of claim 16 wherein the sealing mechanism includes a compressible gasket having a central hole therethrough and a mechanism for compressing said gasket so as to close its central hole.

19. The device of claim 1 wherein the tube has a flared proximal end and an annular shoulder adjacent thereto with a hub seat therebetween, and wherein the hub is provided with a attachment member that is adapted to seat between the flared proximal end and the shoulder of the tube.

20. The device of claim 19 which includes a gasket that is adapted to seal the attachment of the hub to the proximal end of the tube against leakage of blood or other fluids.

21. The device of claim 20 wherein the attachment member is adapted to rotate with respect to the gasket so that the side port may rotate about the axis of the tube.

* * * * *